United States Patent
Devic

(10) Patent No.: US 6,509,486 B2
(45) Date of Patent: Jan. 21, 2003

(54) PROCESS FOR THE SYNTHESIS OF 2-CARBOXYANTHRAQUINONE BY OXIDATION OF 2-ETHYLANTHRAQUINONE WITH NITRIC ACID

(75) Inventor: Michel Devic, Sainte Foy les Lyon (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/987,045

(22) Filed: Nov. 13, 2001

(65) Prior Publication Data

US 2002/0058826 A1 May 16, 2002

(30) Foreign Application Priority Data

Nov. 13, 2000 (FR) .............................. 00 14545

(51) Int. Cl.[7] .............................. C07C 50/18
(52) U.S. Cl. ..................................... 552/264
(58) Field of Search ......................... 552/265

(56) References Cited

FOREIGN PATENT DOCUMENTS

| GB | 662 139 | 12/1951 |
|----|---------|---------|
| GB | 1 425 692 | 2/1976 |
| JP | 50-047964 | 10/1976 |

OTHER PUBLICATIONS

Porshakova et al, Alkylation of anthracene with alcohols, Oct. 23, 1972, Chem. Abs., vol. 77 No. 17, p. 424.*

Chemical Abstracts, vol. 77, No. 17, Oct. 23, 1972 Columbus, Ohio, US; abstract No. 114111g, K.I. Porshakova et al. "Alkylation of anthracene with alcohols in the presence of zinc chloride" p 424.

* cited by examiner

*Primary Examiner*—Alton N. Pryor
(74) *Attorney, Agent, or Firm*—Smith, Gambrell & Russell, LLP

(57) ABSTRACT

The present invention relates to a process for the synthesis of 2-carboxyanthraquinone from 2-ethylanthraquinone by oxidation of the said ethyl group by means of a nitric acid solution. Anthra-quinones are used in the manufacture of oxygen-absorbing films which make possible the preparation of packagings suited to the preservation of oxygen-sensitive products, such as foodstuffs.

11 Claims, No Drawings

PROCESS FOR THE SYNTHESIS OF 2-CARBOXYANTHRAQUINONE BY OXIDATION OF 2-ETHYLANTHRAQUINONE WITH NITRIC ACID

FIELD OF THE INVENTION

The present invention relates to a process for the synthesis of 2-carboxyanthraquinone from 2-ethylanthraquinone by oxidation of the said ethyl group by means of a nitric acid solution.

BACKGROUND OF THE INVENTION

Anthraquinones are used in the manufacture of oxygen-absorbing films which make possible the preparation of packagings suited to the preservation of oxygen-sensitive products, such as foodstuffs.

This is because numerous foodstuffs decompose on contact with oxygen. A packaging comprising a multilayer structure is generally used for their preservation. This multilayer structure comprises, inter alia, an oxygen-barrier film and an oxygen-absorbing film. These films are positioned so that the oxygen-barrier film is in contact with the air external to the sealed packaging and the oxygen-absorbing film is positioned in contact with the food found inside the sealed packaging.

While the aim of the barrier film is to provide for protection against the entry of oxygen inside the sealed packaging, the oxygen-absorbing film provides for the absorption of the oxygen which has possibly remained trapped inside the packaging during the closure of the latter or which is given off by the foods themselves.

The multilayer structure also comprises other films, for example made of polyethylene or of polypropylene, which provide for the mechanical strength of the structure and protection against moisture.

Several processes for the preparation of 2-carboxyanthraquinone are already described by oxidation of anthraquinone or anthracene derivatives. Patent JP 50047964 discloses the preparation of 2-carboxyanthraquinone by oxidation of 2-methylanthraquinone by oxygen in the presence of cobalt and manganese in acetic acid.

However, the known processes for the preparation of 2-carboxyanthraquinone make use of oxidizing agents which are highly toxic to the environment, such as, for example, chromium, manganese and cobalt, or else of techniques or of reactants which are difficult to employ, such as, for example, UV radiation or chlorine.

Furthermore, these processes for the manufacture of 2-carboxyanthraquinone have the disadvantage of using expensive starting materials which are mainly available in small amounts, such as anthracene derivatives or 2-methylanthraquinone.

The invention is thus targeted at providing a solution to these disadvantages.

DETAILED DESCRIPTION OF INVENTION

The invention relates to a process for the synthesis of 2-carboxyanthraquinone from 2-ethylanthraquinone by oxidation with nitric acid.

According to one embodiment of the invention, the oxidation with nitric acid is carried out using an aqueous nitric acid solution at a concentration of between 1 and 20% by weight and preferably between 3 and 15% by weight.

According to one embodiment of the invention, the proportion of 2-ethylanthraquinone to be treated is between 2 and 20% by weight of nitric acid solution and preferably between 5 and 12% by weight.

According to one embodiment of the invention, the reaction temperature is between 120 and 220° C. and preferably between 160 and 200° C.

According to one embodiment of the invention, the pressure at which the reaction is carried out is between 6 and 80 bar and preferably between 15 and 20 bar.

According to one embodiment of the invention, the pressure is kept constant throughout the reaction.

According to one embodiment of the invention, the nitrogen oxide vapours produced during the reaction are recycled as nitric acid.

The process for the manufacture of 2-carboxyanthraquinone will now be described.

The principle of the reaction consists in bringing together 2-ethylanthraquinone and an aqueous nitric acid solution under hot conditions and at a certain pressure. The reaction products are 2-carboxyanthraquinone, carbon dioxide and nitrogen oxides.

The reaction temperature, for its part, is between 120 and 220° C. It is preferably between 160 and 200° C.

The pressure, for its part, is greater than or equal to the saturated vapour pressure of the nitric acid solution at the reaction temperature. If no degassing is carried out, the pressure is greater than the saturated pressure since the reaction generates gaseous compounds, which are carbon dioxide and nitrogen oxides. The reaction is carried out at a pressure which can be between 6 and 80 bar. The pressure is advantageously between 15 and 20 bar, with one or more manual or automatic degassings during the reaction, for a reaction temperature of between 180 and 200° C.

The concentration of the aqueous nitric acid solution, for its part, is from 1 to 20% by weight and it is preferably between 3 and 15% by weight.

The amount of 2-ethylanthraquinone introduced into the reaction medium, for its part, is between 2 and 20% by weight of nitric acid solution and preferably between 5 and 12% by weight.

The reaction can be carried out:

by a batchwise method, that is to say by charging the reactants and discharging the products in a batchwise fashion;

by a semicontinuous method, that is to say by continuous charging of the reactants and batchwise discharging of the products; or alternatively by a continuous method, that is to say by charging the reactants and discharging the products in a continuous fashion.

A batchwise method is preferably used for small amounts of reactants and products. For implementation on an industrial or semi-industrial scale, the semicontinuous or continuous methods are preferred, the semicontinuous method having the advantage of making possible good control of the exothermicity of the reaction and of the concentration of nitric acid and easy discharging of 2-carboxyanthraquinone.

During the reaction, the nitric acid is preferably introduced into the reactor in the form of a concentrated solution of 58 to 60% by weight. This makes it possible to maintain a strength of 3 to 15% by weight of nitric acid in the reaction medium.

The duration of the reaction depends on the temperature at which the reaction is carried out. When the reaction is carried out at 190° C. under the conditions set out above, the reaction lasts between 30 minutes and 1 hour.

It is important for the stirring to be efficient in order to ensure good emulsification of the molten 2-ethylanthraquinone (example: 2-ethylanthraquinone melts at approximately 110° C.) in the aqueous nitric acid solution and good entry into suspension of the 2-carboxyanthraquinone formed, which is solid at the reaction temperature (M.p.≅290° C.).

The reactor can be made of stainless steel or of enamelled steel.

During the reaction, nitrogen oxides given off can either be removed or recycled as nitric acid after oxidation using air or oxygen under pressure.

On completion of the reaction, the 2-carboxyanthraquinone is isolated by filtering the reaction medium. The filtrate, which is a relatively pure nitric acid solution, can be reused after adjusting its nitric acid strength by addition of concentrated nitric acid. The amount of aqueous effluents is thus substantially reduced.

The 2-carboxyanthraquinone produced is very pure, at approximately 99%, and only requires washing with water, preferably tepid water, until the pH is neutral, the sign of the removal of any residual nitric acid.

The melting point of the 2-carboxyanthraquinone is subsequently measured, which melting point must be between 287 and 297° C., ensuring a satisfactory degree of purity, and preferably between 292 and 296° C.

EXAMPLES

The invention will now be described by non-limiting examples.

Example 1

An example of a process for the synthesis of 2-carboxyanthraquinone from 2-ethylanthraquinone according to a batchwise method as defined above will now be described.

A 1000 cm$^3$ stainless steel autoclave, provided with an internal PTFE sleeve and equipped with a stirrer turbine, with an internal coil for cooling with water and with an external electric heating sleeve, is used.

600 g of a 15% by weight aqueous nitric acid solution and 58.2 g of 2-ethylanthraquinone are charged under cold conditions. The mixture is heated to 190° C. with stirring at 1000 revolutions/min while maintaining the pressure at between 15 and 20 bar by successive degassings. The temperature is thus maintained at 190° C. for 1 hour under a pressure of 15 to 20 bar and then the reactor is cooled and decompressed. The reaction mixture is filtered through a sintered glass filter and washed with hot demineralized water until the filtrate is at a pH=6. The washed precipitate is subsequently dried for 24 hours in a ventilated oven at 120° C.

57.2 g of 2-carboxyanthraquinone with a melting point of 293 to 294° C. are finally obtained. The chemical yield of the reaction is 92.7% and NMR analysis shows that the product has a purity of greater than 99%.

Example 2

An example of a process for the synthesis of 2-carboxyanthraquinone from 2-ethylanthraquinone according to a semicontinuous method as defined above will now be described.

A 1200 cm$^3$ reactor equipped with a 750 revolutions/min stirrer with oblique paddles, everything being made of Hastelloy C22, is used to carry out the reaction.

The reactor is subsequently charged under cold conditions with 470 g of demineralized water and 59 g of 2-ethylanthraquinone. Heating is begun and the stirrer is started. The reaction is carried out at 180° C. and the pressure is regulated so as not to exceed 15 bar. 160 g of 58% nitric acid are injected into the reaction medium at 180° C. using a pump. The pump is adjusted so that the injection is carried out gradually and continuously over a period of time of approximately 30 minutes. The reaction is subsequently carried out for a further 30 minutes after the end of the injection, the reaction medium is then allowed to return to ambient temperature and the reactor is decompressed. After filtering the reaction medium, the solid recovered is washed with hot demineralized water until the aqueous wash liquors are neutral and then dried in an oven at 120° C.

This reaction makes it possible to obtain 60.7 g of 2-carboxyanthraquinone, i.e. a chemical yield of 96%.

The invention makes it possible to obtain at a low cost a large amount of 2-carboxyanthraquinone by virtue of a process of synthesis which is easy to implement and which uses inexpensive reactants.

The process of synthesis described above also makes possible the recycling of the effluents, reducing in this way the raw material costs and avoiding the expense of reprocessing the waste.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing reference is hereby incorporated by reference.

What is claimed is:

1. Process for the synthesis of 2-carboxy-anthraquinone comprising oxidizing 2-ethylanthraquinone with nitric acid to form said 2-carboxy-anthraquinone.

2. Process according to claim 1, wherein the oxidation with nitric acid is carried out using an aqueous nitric acid solution at a concentration of, in the reaction medium, between 1 and 20% by weight.

3. Process according to claim 1, wherein the proportion of 2-ethylanthraquinone to be treated is between 2 and 20% by weight of nitric acid solution.

4. Process according to claim 1, wherein the oxidizing of the 2-ethylanthraquinone is conducted at a reaction temperature of between 120 and 220° C.

5. Process according to claim 1, wherein the oxidizing of the 2-ethylanthraquinone is conducted at a pressure of between 6 and 80 bar.

6. Process according to claim 5, wherein the pressure is kept substantially constant throughout the reaction.

7. Process according to claim 1, wherein nitrogen oxide vapors produced during the reaction are recycled as nitric acid.

8. Process according to claim 2, wherein the amount of nitric acid is between 3 and 15% by weight.

9. Process according to claim 3, wherein the amount 2-ethylanthraquinone is between 5 and 12% by weight.

10. Process according to claim 4, wherein the reaction temperature is between 160 and 200° C.

11. Process according to claim 5, wherein the reaction pressure is between 15 and 20 bar.

* * * * *